US009475025B2

(12) United States Patent
Samper et al.

(10) Patent No.: US 9,475,025 B2
(45) Date of Patent: Oct. 25, 2016

(54) MICROFLUIDIC HANDLING SYSTEM (75) Inventors: Victor Donald Samper, Kirchseeon (DE); Christoph Boeld, Munich (DE); Christian Friedrich Peter Rensch, Munich (DE); Ruben Julian Horvath-Klein, Munich (DE)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 1009 days.

(21) Appl. No.: 13/340,317

(22) Filed: Dec. 29, 2011

(65) Prior Publication Data
US 2013/0170931 A1 Jul. 4, 2013

(51) Int. Cl.
G06F 7/00 (2006.01)
B01J 19/00 (2006.01)
G01N 35/04 (2006.01)
G01N 35/00 (2006.01)

(52) U.S. Cl.
CPC ..... *B01J 19/0093* (2013.01); *G01N 35/00029* (2013.01); *G01N 35/04* (2013.01); *B01J 2219/0081* (2013.01); *B01J 2219/00986* (2013.01); *G01N 2035/0425* (2013.01)

(58) Field of Classification Search
USPC ........................................................ 700/214
See application file for complete search history.

(56) References Cited

U.S. PATENT DOCUMENTS

| 6,025,985 | A * | 2/2000 | Leytes et al. ............ 361/679.21 |
| 7,303,727 | B1 | 12/2007 | Dubrow et al. |
| 7,745,207 | B2 | 6/2010 | Jovanovich et al. |
| 7,829,032 | B2 | 11/2010 | Van Dam et al. |
| 8,403,906 | B2 | 3/2013 | Buck et al. |
| 2005/0013747 | A1 * | 1/2005 | Huynh-Ba et al. ............ 422/104 |
| 2007/0184546 | A1 * | 8/2007 | Farrelly et al. ............ 435/286.3 |
| 2008/0104993 | A1 * | 5/2008 | Zenobi et al. ................ 62/440 |
| 2008/0140046 | A1 * | 6/2008 | Buck et al. .................... 604/407 |
| 2010/0035349 | A1 | 2/2010 | Bau et al. |
| 2010/0279309 | A1 | 11/2010 | Sui |
| 2011/0054679 | A1 * | 3/2011 | Lefebvre et al. ............ 700/245 |
| 2011/0097245 | A1 | 4/2011 | Elizarov et al. |
| 2011/0150714 | A1 * | 6/2011 | Elizarov et al. ............ 422/159 |
| 2011/0207621 | A1 | 8/2011 | Montagu et al. |

FOREIGN PATENT DOCUMENTS

| EP | 1355160 A1 | 10/2003 |
| EP | 2093571 A2 | 8/2009 |
| GB | 2386153 A | 9/2003 |
| WO | 9852047 A1 | 11/1998 |
| WO | 0211887 A1 | 2/2002 |
| WO | 2006105936 A1 | 10/2006 |

OTHER PUBLICATIONS

Search Report and Written Opinion from corresponding PCT Application No. PCT/US2012/070433 dated Apr. 29, 2013.

* cited by examiner

*Primary Examiner* — Kyle Logan
(74) *Attorney, Agent, or Firm* — Fletcher Yoder, P.C.

(57) ABSTRACT

Techniques and devices are provided related to a handling system for cassettes for radiolabeled compound synthesis that include a magazine that is unshielded and that is configured to receive a plurality of microfluidic synthesis cassettes. In one embodiment, the plurality of microfluidic synthesis cassettes include nonradioactive reagents to generate a radiolabeled compound when reacted with a radioactive species. In this manner, a cassette handling device may be stored unshielded and may be coupled to a cassette handling platform to allow advancement of the plurality of microfluidic synthesis cassettes into the cassette handling platform and, in turn, a shielded radiosynthesis machine.

20 Claims, 7 Drawing Sheets

MICROFLUIDIC HANDLING SYSTEM

BACKGROUND

Radiopharmaceuticals are used in a wide range of medical applications. For example, radiopharmaceuticals may be used to generate medical images in a number of imaging modalities, such as Positron Emission Tomography (PET) and Single Photon Emission Computed Tomography (SPECT). PET and SPECT are classified as "nuclear medicine" because they are often used in conjunction with a radioactive tracer that is injected into a patient and that facilitates image acquisition. After the radioactive tracer, or radiopharmaceutical, is injected, it is absorbed by the blood or a particular organ of interest. The patient is then moved into the PET or SPECT detector that measures the emission of the radiopharmaceutical and creates an image based on the characteristics of the detected emission. In addition, radiopharmaceuticals may be used to treat patients. Examples of radiopharmaceuticals include FDG (2-[$^{18}$F]-fluoro-2-deoxyglucose), other $^{18}$F based fluorinated tracers, $^{13}$N ammonia, $^{11}$C based tracers, $^{15}$O gas, and $^{15}$O water, and others.

The half lives of many of these radiopharmaceuticals range from two minutes to two hours. Thus, the injection into the patient and any subsequent imaging generally take place within a very short time period after production of the radiopharmaceutical. Accordingly, these radiopharmaceuticals are often synthesized at on-site facilities or in local production facilities within suitable driving distance of the patient care site to prevent undue decay of the radiopharmaceutical prior to use. Accordingly, because of the distributed nature of radiopharmaceutical production, it is desirable to provide small-batch synthesis techniques that yield consistent results and suitable safety profiles when operated by technicians spread out over a number of facilities.

BRIEF DESCRIPTION

In one embodiment, a cassette handling device for dispensing cassettes for radiolabeled compound synthesis is provided. The cassette handling device includes a first microfluidic synthesis cassette comprising nonradioactive reagents to generate a first radiolabeled compound when contacted with a first radioactive molecule and a second microfluidic synthesis cassette comprising nonradioactive reagents to generate a second radiolabeled compound when contacted with a second radioactive molecule. The cassette handling device may also include a magazine having first and second slots accommodating the first and second microfluidic synthesis cassettes, respectively. Further, the cassette handling device may also have an interface adapted to couple the magazine to a cassette handling platform configured to receive the first and second microfluidic synthesis cassettes in series, wherein the cassette handling platform is configured to operatively couple to a radiosynthesis device, and wherein the radiosynthesis device is shielded and the cassette handing device is unshielded.

In another embodiment a magazine for storing cassettes for radiolabeled compound synthesis is provided that includes an unshielded housing having a plurality of slots configured to accommodate microfluidic synthesis cassettes and a plurality of microfluidic synthesis cassettes disposed respectively in the plurality of slots, wherein the plurality of microfluidic synthesis cassettes include nonradioactive reagents to generate a radiolabeled compound when contacted with a radioactive species. The magazine may also include a coupling configured to couple the magazine to a shielded cassette handling platform, wherein the coupling is configured to allow advancement of the plurality of microfluidic synthesis cassettes into the shielded cassette handling platform.

In another embodiment a cassette handling device for dispensing cassettes for radiolabeled compound synthesis is provided. The cassette handling device includes a magazine having an unshielded housing and a plurality of slots configured to accommodate microfluidic synthesis cassettes. The cassette handling device may also include a plurality of microfluidic synthesis cassettes disposed respectively in the plurality of slots, wherein the plurality of microfluidic synthesis cassettes include nonradioactive reagents. Further, the cassette handling device may also include a coupling configured to couple the cassette handling device to a cassette handling platform, wherein the coupling is configured to allow advancement of the plurality of microfluidic synthesis cassettes into the cassette handling platform, wherein the cassette handling platform is configured to operatively couple to a radiosynthesis device, and wherein the radio synthesis device is shielded and the cassette handing device is unshielded.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

The present disclosure relates to a microfluidic handling system that may be used in conjunction with microfluidic cassettes configured to synthesize radioactive compounds in a medical setting. In particular embodiments, the handling system may operate according to a jukebox concept. The handling system may load a new cassette into a synthesizer as needed and according to a desired end compound. The cassettes include reagents and/or reaction conditions for the synthesis of the radiopharmaceutical. After use, the cassette is ejected from the system and a new cassette may be loaded into the synthesizer.

Radiopharmaceutical production is relatively complex and involves specialized equipment and skilled personnel. Many parts of a system for synthesizing such compounds are shielded in heavily reinforced structures. The use of microfluidic cassettes for radiopharmaceutical production facilitates smaller-scale production of compounds at the point of use, which in turn may allow production of such compounds in smaller facilities and with smaller synthesis machines. Provided herein are techniques for improving storage and handling of such cassettes to reduce radioactive waste and reduce the size of the overall system, which may result in more efficient production of radiopharmaceuticals. A disposable microfluidic cassette that is used in conjunction with the present techniques may be stored within a magazine of multiple cassettes as part of a microfluidic handling device. The magazines may be configured with a plurality of identical individual cassettes, where a new cassette is used each time the synthesis process runs. Alternatively, a magazine may include different types of cassettes, each configured to synthesize a different type of radiopharmaceutical, and with the system, responding to a user input, inserting the appropriate unit for the desired process. Further, each dispenser may be used with one or more magazines. The techniques provided herein facilitate multi-run capability for a radiopharmaceutical synthesizer that interfaces with a particle accelerator. In particular, because the dispenser may store multiple cassettes, the cassettes may be automatically reloaded after each run, which reduces the amount of technician intervention with the device.

In particular embodiments, the microfluidic handling system includes a fluid handling magazine and/or individual cassettes that are designed to facilitate high density cassette storage in a storage rack, automated handling to and transfer from the storage rack to the processing system, e.g., a synthesizer in the case of an automated PET radiochemistry system, and loading into and ejection from the processing system to a waste holder and loading of the next unit cassette. The cassette is self-contained to chemicals or material specific to the selected process and stored on the cassette. In addition, the cassette may be tagged or labeled with identification information or processing or handling instructions for utilizing the cassette to streamline compound synthesis. The identification information may be read and/or stored by a recognition unit associated with the device. Further, the identification information may be used for selection or inventory for the magazines. Based on a user input, the device may select the appropriate cassette or may present a menu of appropriate cassettes.

The present techniques may reduce synthesizer under utilization as a result of residual activity in the synthesizer or associated components. This residual activity may prevent users from opening the hot cell or radioactive portion of the synthesizing device to load in the next cassette for the next synthesis run. In accordance with the present techniques, the microfluidic dispensing system as provided includes an automatic handling step that allows the next cassette to be loaded even when residual activity is high. In addition, the separation of the cold (i.e., nonradioactive) portion that stores the cassettes from the hot synthesizer portion allows a user to select the appropriate cassette without exposure to residual synthesizer activity. Further, reloading the synthesizer via a magazine may provide faster reloading, which may reduce interaction with the hot portion of the device, even in embodiments in which a cassette is manually loaded from the magazine 12. Further, such systems may also provide the benefit of more efficient waste handling. In one embodiment, waste is stored on the cassette. Accordingly, ejecting a cassette into a shielded waste container removes all residual activity from the hot cell. This allows the user to open the hot cell as soon as the process is complete.

Figure 1:
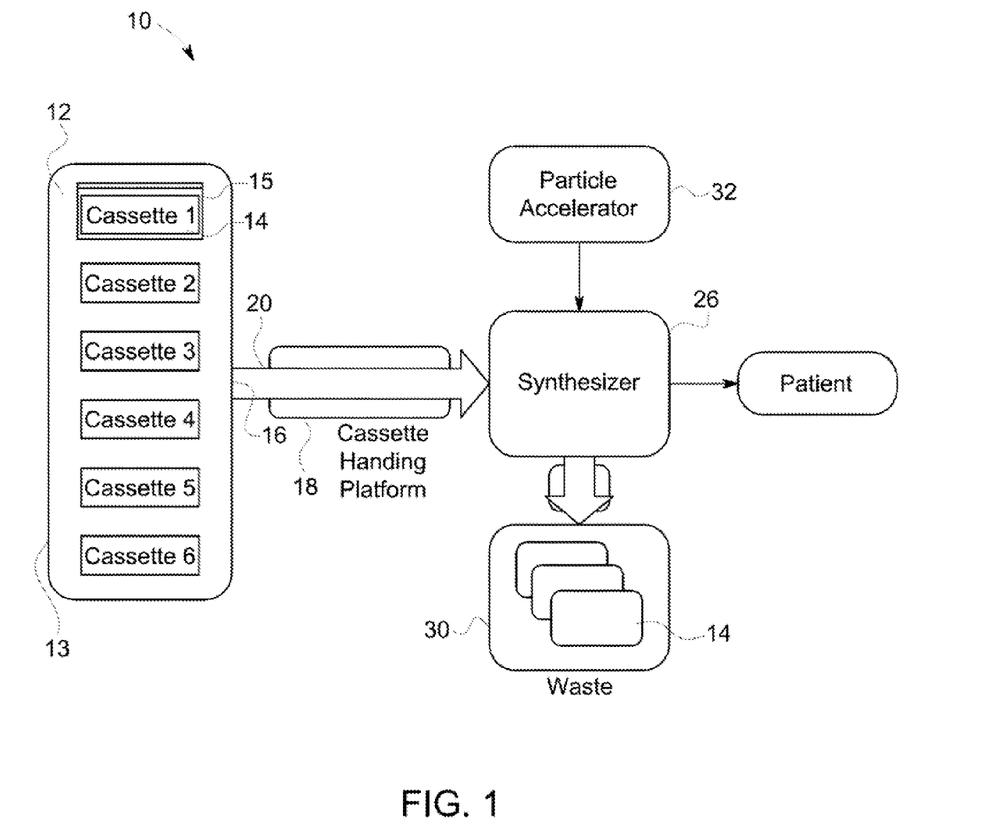
FIG. 1 is a block diagram of a system for radiocompound synthesis in accordance with aspects of the present disclosure.

Turning to the figures, FIG. 1 is a block diagram of a radiocompound synthesis system 10 that may be used in conjunction with the present techniques. The system includes a magazine 12 that stores a plurality of cassettes 14 in accommodating slots 15. The cassettes are stored cold, i.e., are nonradioactive, in the magazine 12, which is also cold and, accordingly, may be implemented with a housing 13 that, in particular embodiments, is unshielded. In other embodiments, the housing 13 may be partially shielded in a portion that interacts with a hot side of the system 10. The cassettes 14 are configured to exit the magazine 12 via one or more exit ports 16 that are shaped to accommodate movement of the cassettes 14 into a cassette handling platform 18 along pathway 20. From the cassette handling platform 18, the cassettes 14 are loaded into the synthesizer 26, which receives radioactive reagents from a particle accelerator 32. Used cassettes 14 are ejected into a waste container 30. The generated radiopharmaceutical may be delivered to the patient for therapy and/or imaging. The system 10 is configured to generate a variety of radiopharmaceuticals, depending on the type of particle accelerator 32 and the cassette availability.

The synthesizer 26, particle accelerator 32, and waste container 30 are all shielded components of the system 10. In the depicted embodiment, the cassette handling platform 18 provides an interface between the cold magazine 12 and the hot synthesizer 26. In such an embodiment, the magazine 12 is separated from any contamination and may be stored cold even after partial use, e.g., after use of some of the cassettes 14. Accordingly, each magazine 12 may have a longer shelf life and may be more inexpensively handled and disposed of. Further, the magazine 12 includes a housing 13 that may be more efficiently manufactured without any shielding components. The cassette handling platform 18 may be part of the synthesizer 26, part of the magazine 12, or a separate component. Further, the cassette handling platform 18 may be shielded or unshielded, depending on the coupling to the synthesizer 26. In one embodiment, the cassette handling platform 18 may include a double door arrangement with a hot side shield door and a cold side unshielded door. After the cassette 14 enters the cassette handling platform 18 from the cold side door, the doors are sealed and negative pressure is applied from the hot side before the hot side door opens and the cassette 14 enters the synthesizer 26. In other embodiments, the magazine 12 may couple directly to the synthesizer 26. In such an embodiment, the synthesizer 26 may provide a shielded interface or coupling to protect the magazine 12 from contamination. The bulkier components of the magazine 12, such as the housing 13, remain uncontaminated and may be disposed of separately from the used cassettes 14, which are generally hot but are also smaller and generate relatively smaller volumes of waste.

Figure 2:
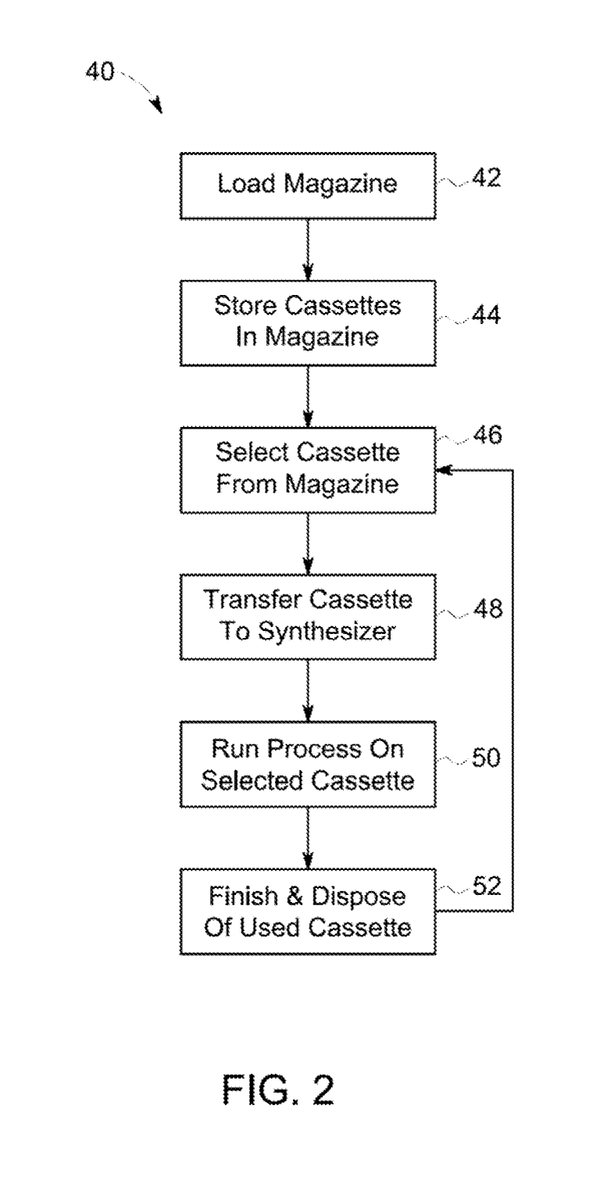
FIG. 2 is a flow diagram of a method of advancing cassettes into a radiocompound synthesizer in accordance with aspects of the present disclosure.

FIG. 2 is a flow diagram of a method 40 of advancing a cassette 14 through the system 10. Certain steps of the method 40 may be implemented manually or automatically. Further, certain steps of the method 40 may be implemented by a processor-based machine including a memory storing instructions for facilitating all or part of a particular step of the method 40. The memory may be any suitable volatile memory device and/or a non-volatile mass-storage device. The processor-based machine may be configured to perform the steps without user intervention or may be configured to receive a user input and execute instructions in response. Accordingly, such machines may include suitable user interface components, including a display and/or user input controls. The instructions may include providing an input to hardware components of the system 10, which may function to mechanically or otherwise physically interact with one or more components of the system 10.

The method starts at step 42, in which individual cassettes 14 are loaded into a magazine 12, manually or by an automated loading machine at step 42. Further, magazines 12 may be loaded on-site or may be provided pre-loaded. One benefit of the present techniques is that, because the magazine is stored cold, the magazine 12 may be loaded or adjusted by technicians on-site with reduced risk of exposure. The cassettes 14 can be inserted into the magazine 12 while in a protective package, or the package can be removed prior to insertion in magazine 12.

The cassettes 14 may be implemented with particular shapes or sizes such that cassettes 14 generating a particular compound or with different content may only be loaded into particular slots 15 in the magazine or in a predetermined orientation or position within the magazine. After loading, the cassettes 14 are stored in the magazine 12 until use at step 44. The magazines 12 may be stored in a rack or may be stored interfaced with the cassette handling platform 18. As needed, the cassette 14 may be selected from the magazine 12 at step 46 and transferred to the synthesizer at step 48. In one embodiment, the cassette 14 may be manually selected and advanced into the synthesizer 26. In another embodiment, an operator may make a selection on a processor-based machine, and the cassette 14 may be automatically transferred to the synthesizer 26 based on instructions provided by the machine.

The cassette 14, once loaded into the synthesizer 26, is processed by the synthesizer at step 50 according to the particular parameters associated with the cassette 14. In certain embodiments, a radioactive reagent generated by the particle accelerator 32 may be injected into one or more channels on the cassette 14 and may undergo various chemical processes until the desired radiopharmaceutical is generated. The used cassette 14, which has residual radioactive activity, is ejected into a shielded waste container 30. The system 10 may return to step 46 if other compounds are desired. Because the cassette 14 is specific to a particular compound, successive runs on the synthesizer 26 may yield different compounds using different types of cassettes 14.

Figure 3:
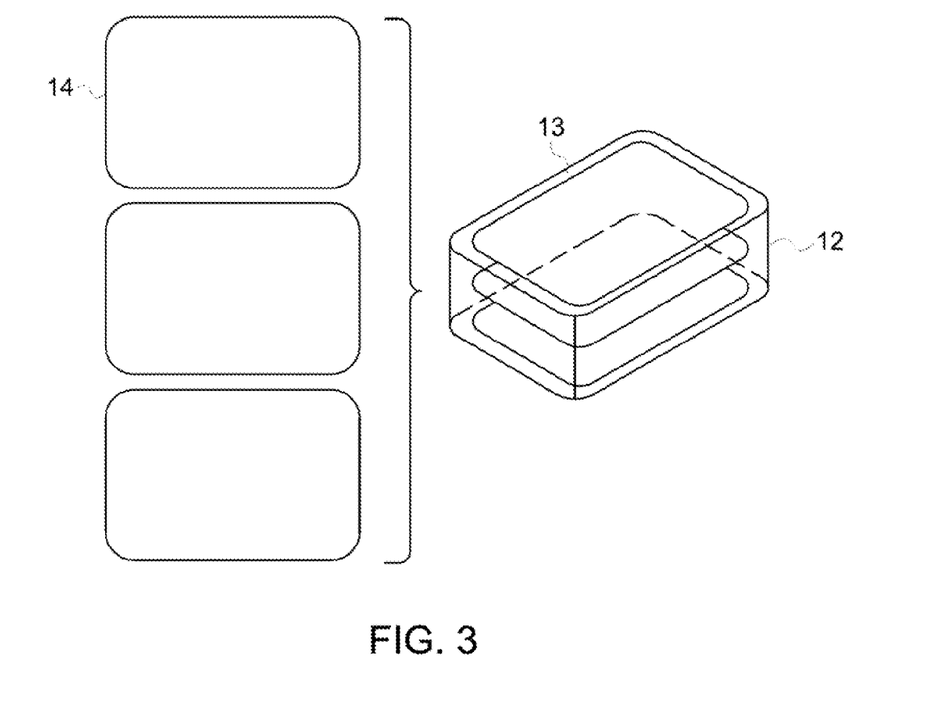
FIG. 3 is a block diagram of a magazine loading configuration in accordance with aspects of the present disclosure.

FIG. 3 is an illustration of a cassette loading arrangement for a magazine 12. In one embodiment, a magazine 12 may be loaded with a plurality of different cassettes 14 in a particular order, each individual cassette 14 corresponding to a scheduled procedure, such as an imaging or treatment procedure, for the treatment facility for a particular day or period of time. As the day progresses, the appropriate cassette 14 may be advanced into the synthesizer 26 in a chronological order corresponding to the appointment schedule and corresponding to their order within the magazine 12. In this manner, radiopharmaceuticals corresponding to the scheduled patients may be generated with reduced employee interaction with the hot portion of the system 10. Further, the magazine 12 may be loaded for the day based in the predetermined appointment schedule. As appointments are changed or cancelled, the magazine 12 may be rearranged. For example, the magazine housing 13 may include a rear panel that opens and allows access to the loaded cassettes 14. One or more cassettes 14 may be easily switched out to account for any changes in the patient schedule.

Figure 4:
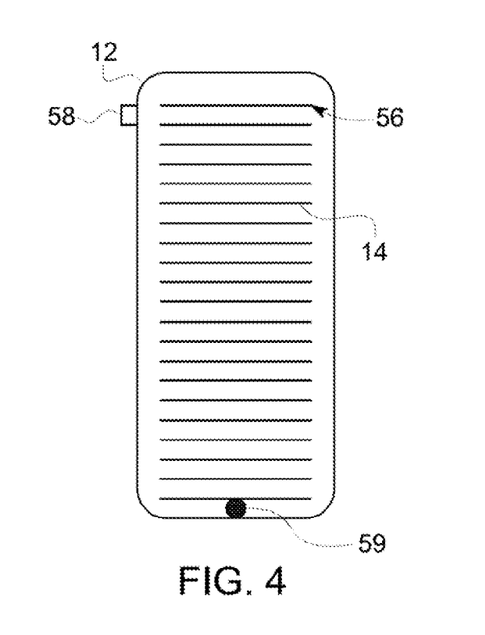
FIG. 4 is a block diagram of an alternative magazine loading configuration in accordance with aspects of the present disclosure.

The cassettes 14 may be loaded into the magazine 12 according to a suitable geometric arrangement and a desired density. FIG. 4 shows cassettes 14 stacked in a generally vertical arrangement. The magazine 12 may include an on-deck position 56 that corresponds with an opening 58 that may be open to the cassette handling platform 18 or the synthesizer 26. In one embodiment, the magazine may only include a single opening 58. Accordingly, only the cassette in the on-deck position may be transferred to the synthesizer 26. The magazine 12 may also contain a spring-loaded device 59 that automatically advances the next cassette 14 into the on-deck position 56 when the previous cassette 14 has exited the magazine 12. In this manner, the magazine 12 may facilitate control of cassette usage by only allowing cassettes 14 to be used in order. In one embodiment, the cassettes 14 may be arranged according to patient schedules. In another embodiment, the cassettes 14 may be arranged according to expiration date, with the oldest cassettes 14 in position to be used before fresher cassettes 14.

Figure 5:
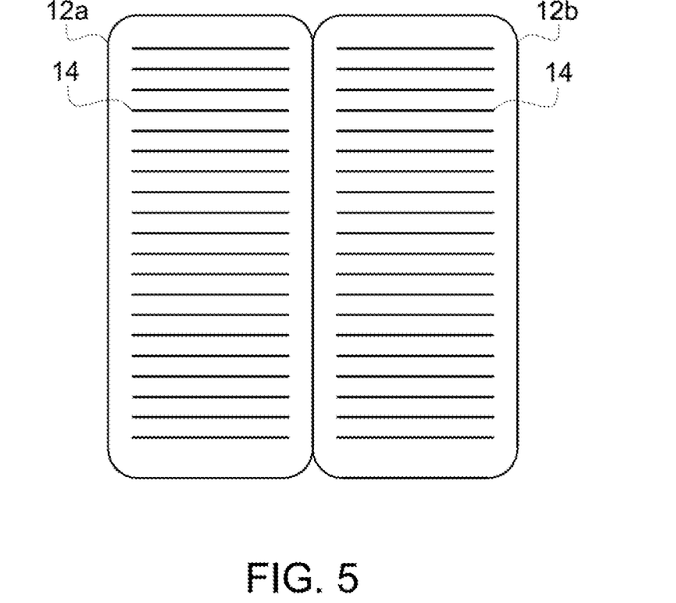
FIG. 5 is a block diagram of an alternative magazine loading configuration in accordance with aspects of the present disclosure.
Figure 6:
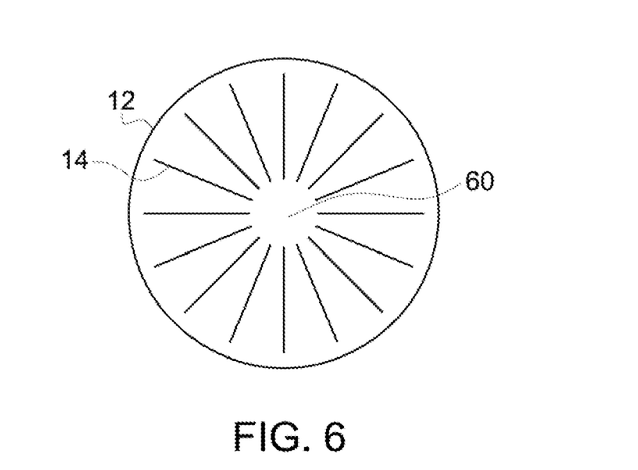
FIG. 6 is a block diagram of an alternative magazine loading configuration in accordance with aspects of the present disclosure.

FIG. 5 illustrates a multi-magazine arrangement with a plurality of magazines 12a and 12b in a linear configuration. For example, each magazine 12a and 12b may feature a single cassette-type or a single group of cassettes 14. FIG. 6 is a carousel-type magazine 12 which may be configured to rotate about a central axis 60. Such an arrangement may be used if the cassettes 14 may benefit from being stored vertically or in rotation, e.g., nonstatic. In one embodiment, the magazine 12 may be configured to store cassettes 14 are shaken or continuously rotated in cases where sedimentation or separation of an agent or material on the cassette 14 can be avoided by non-static storage. Other examples of possible arrangements include stacked carousels and arc segment shaped magazines 12. The cassettes 14 and magazines 12 may be identified by a bar code, a magnetic strip, an optical tag, an RFID, a color, a physical shape, a text label, an electronic label, their physical location in the magazine, or any other unique identifying feature. The system 10 may include a reader for reading the identification information and updating a magazine inventory.

The magazine 12 may also be implemented to provide a particular environment for the cassette 14. For example, the magazine 12 may provide a cooled, room temperature, or heated environment. Further, the magazine 12 may store cassette 14 in a sterile or non-sterile environment. Other environmental conditions facilitated by the magazine 12 may include application of a magnetic field, a particular pressure, or light. Further, subenvironments may be created within a single magazine 12. In one embodiment, a protective cover or bag over an individual cassette 14 may separate a cassette 14 from the general environment of the magazine. In another embodiment, the magazine 12 may be separated into different environmental zones. Because the magazines 12 are implemented without shielding and are not exposed to residual radioactive activity, such environmental modifications may be incorporated into the magazine 12 without having to overcome the properties of any inherent shielding within the housing 15.

Figure 7A:
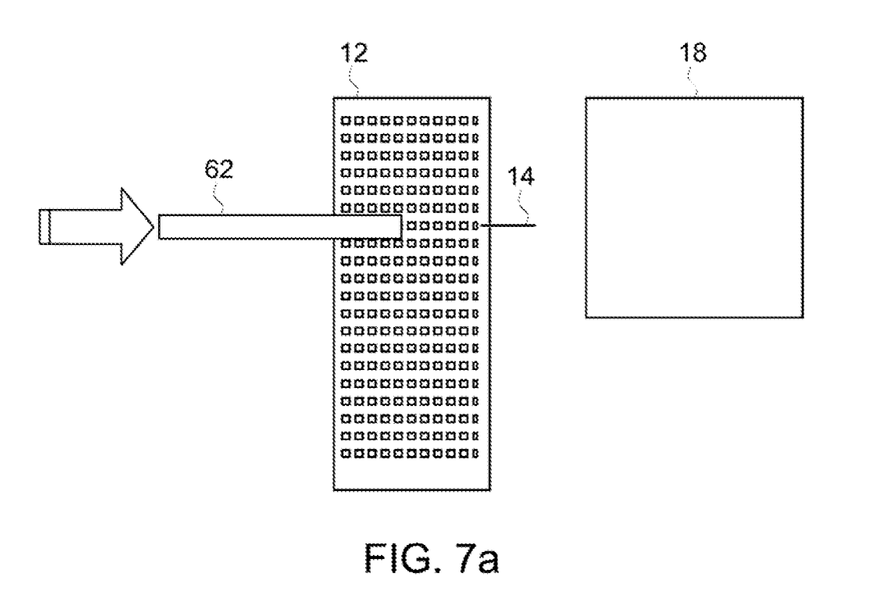
FIG. 7A is an illustration of a transfer device coupled to an individual cassette for loading into a cassette handling platform in accordance with aspects of the present disclosure.
Figure 7B:
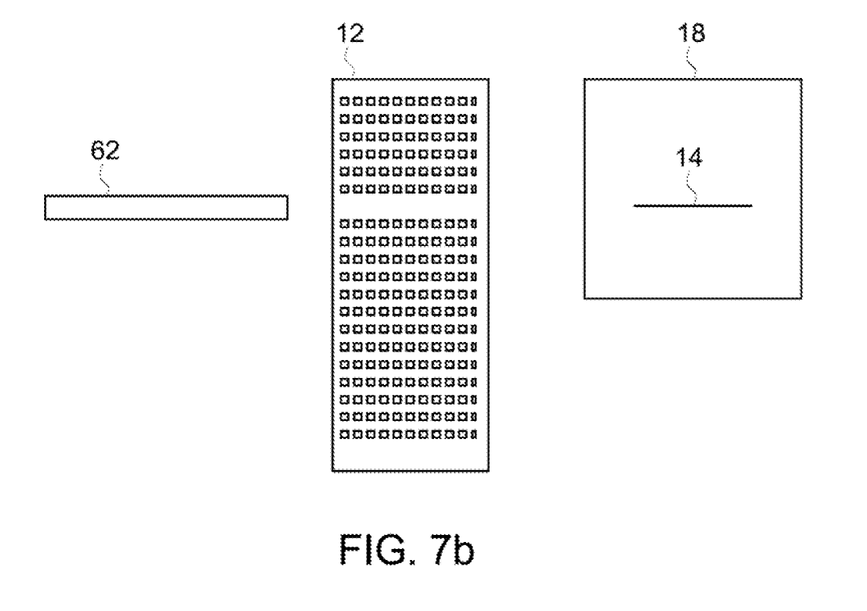
FIG. 7B is an illustration of a transfer device loading an individual cassette into the cassette handling platform in accordance with aspects of the present disclosure.

FIGS. 7A and 7B show transfer of the cassette 14 from the magazine 12 to the cassette handling platform 18. In certain embodiments, the cassette handling platform 18 may be coupled to or part of the synthesizer 26. A transfer element 62 or multiple transfer elements 62 or robotic assemblies may facilitate the transfer. The transfer element 62 may push the selected cassette 14 into the cassette handling platform 18. The transfer element 62 may remove the selected cassette 14 from the magazine 12 and load it into the cassette handling platform 18 in a translational motion, as shown in FIG. 7B. In particular embodiments, the transfer element 62 may couple to the cassette 14 by vacuum, gravity, mechanical interlock, magnetism, pneumatic, or electrostatic attraction. The cassette 14 may be be loaded directly into the cassette handling platform 18 (or synthesizer 26) or may be transferred to a second transfer mechanism, such as rails or a belt or a drawer that transfers the cassette into the instrument. The transfer process may also include an unpacking step if the cassette 14 is stored packaged in the magazine 12. The transfer element 62 may also transfer a cassette 14 in a bag that provides a local environment and that not removed during subsequent processing. The transfer process may also include a step for sterilisation such as gamma or chemical sterilization.

Figure 8:
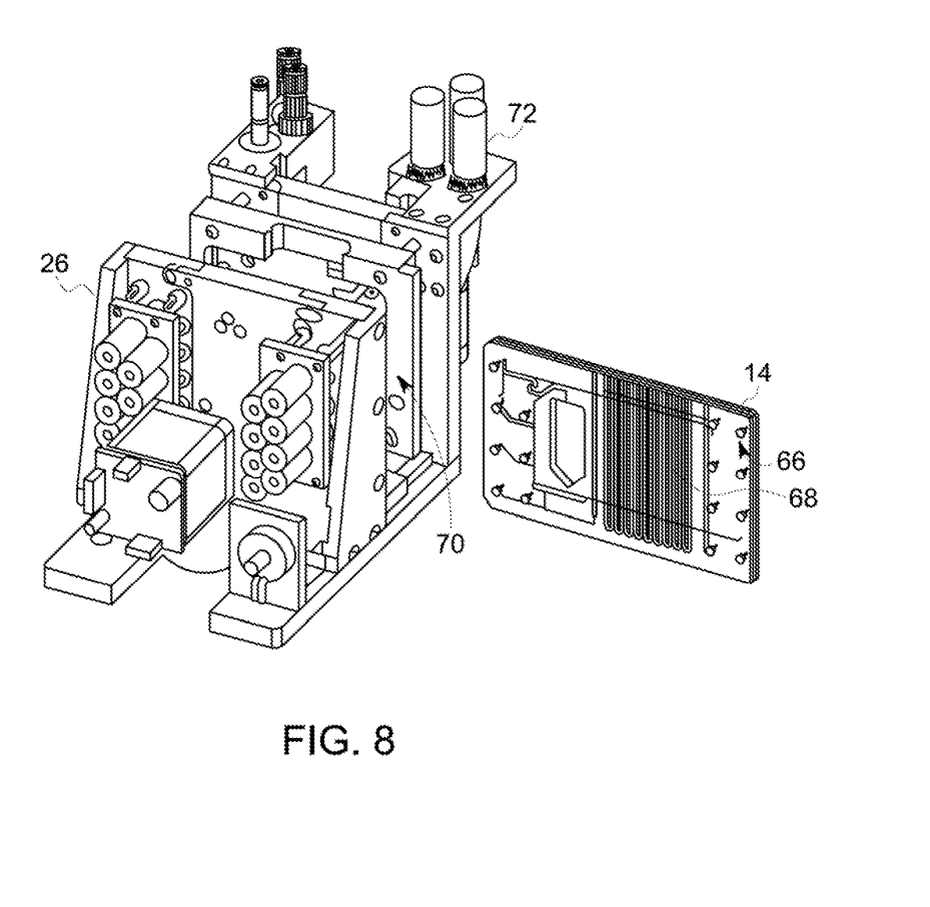
FIG. 8 is an illustration of a transfer device loading an individual cassette into the cassette handling platform in accordance with aspects of the present disclosure.

The transfer element 62, magazine 12, and cassette handling platform 18 or synthesizer 26 may be configured such that one or more may translate and/or rotate to facilitate transfer. FIG. 8 is an illustration of a synthesizer 26 and a cassette 14. The cassette 14 may be rotated or translated to align the appropriate reagent reservoirs 66 and/or channels 68 with the entry passage 70. The synthesizer 26 may also be configured to receive the radioactive reagent 72 from the particular accelerator.

Figure 9:
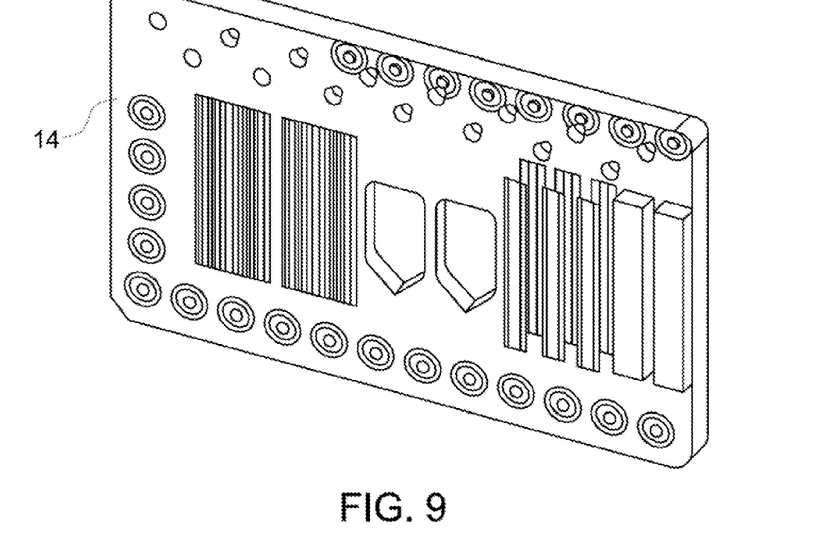
FIG. 9 is an illustration of an individual single process cassette in accordance with aspects of the present disclosure.
Figure 10:
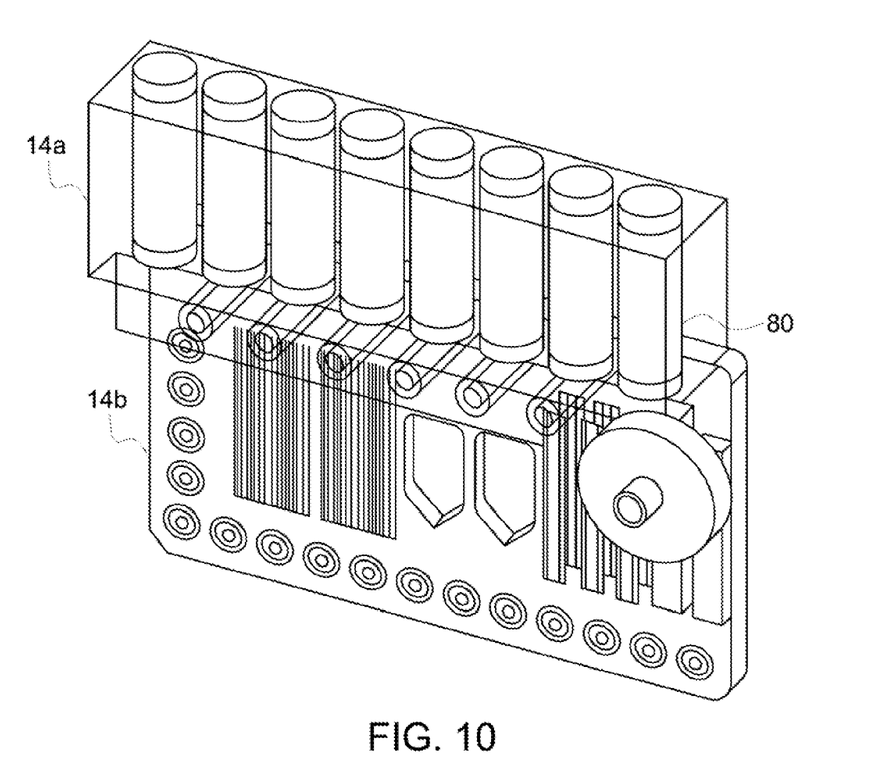
FIG. 10 is an illustration of a single process cassette combined with a single reagent storage cassette in accordance with aspects of the present disclosure.

In one embodiment, the transfer process may be configured to transfer multiple cassettes 14, such as multiple processing cassettes for complex processes, or processing cassettes with reagent storage cassettes. FIG. 9 shows a single process cassette 14. FIG. 10 shows a reagent storage cassette 14a coupled to a single process cassette 14b. Further, multiple cassettes 14 may be loaded sequentially, may feed multiple instruments, or may run in parallel from a single or multiple magazines 12, e.g., in a cluster arrangement.

The technical effects of the disclosed embodiments include increased throughput and higher utilization of hardware, the increase in available processes possible within a working day, and the improved process quality. Further, existing PET tracer producers may increase output by implementing the disclosed techniques.

The present disclosure provides examples, including the best mode, and enables any person skilled in the art to practice the techniques disclosed herein, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A cassette handling device for handling cassettes for radiolabeled compound synthesis comprising:
a first microfluidic synthesis cassette comprising nonradioactive reagents to generate a first radiolabeled compound when reacted with a first radioactive species;
a second microfluidic synthesis cassette comprising nonradioactive reagents to generate a second radiolabeled compound when reacted with a second radioactive species;
a magazine comprising first and second slots accommodating the first and second microfluidic synthesis cassettes, respectively; and
an interface adapted to couple the magazine to a cassette handling platform configured to receive the first or second microfluidic synthesis cassettes, wherein the cassette handling platform is configured to operatively couple to a radiosynthesis device, and wherein the radiosynthesis device is shielded and the cassette handling device is unshielded.

2. The cassette handling device of claim 1, comprising a shielded waste area.

3. The cassette handling device of claim 1, wherein the magazine comprises only one opening coupled to the cassette handling platform.

4. The cassette handling device of claim 1, wherein the magazine comprises a first opening coupling the first microfluidic synthesis cassette to the cassette handling platform and a second opening coupling the second microfluidic synthesis cassette to the cassette handling platform.

5. The cassette handling device of claim 1, wherein the magazine comprises a spring-loaded device that advances the first or second microfluidic synthesis cassette into the cassette handling platform.

6. The cassette handling device of claim 1, wherein the first slot and the second slot are different shapes such that the first microfluidic synthesis cassette cannot be loaded into the second slot.

7. The cassette handling device of claim 1, wherein the magazine is configured to store the first microfluidic synthesis cassette and the second microfluidic synthesis cassette at different temperatures.

8. The cassette handling device of claim 1, wherein the magazine is configured to store the first microfluidic synthesis cassette or the second microfluidic synthesis cassette in a bag that provides a local environment.

9. The cassette handling device of claim 1, comprising:
a controller coupled to the cassette handling device, wherein the controller comprises:
a memory storing one or more routines; and
a processing component configured to execute the one or more routines stored in the memory, wherein the one or more routines, when executed by the processing component causes acts to occur, comprising:
receiving a user input;
selecting the first microfluidic synthesis cassette or the second microfluidic synthesis cassette based on the user input; and
providing instructions to advance the first microfluidic synthesis cassette or the second microfluidic synthesis cassette into the cassette handling platform based on the user input.

10. The cassette handling device of claim 9, wherein the cassette handling device comprises a transfer device for advancing the first microfluidic synthesis cassette or the second microfluidic synthesis cassette into the cassette handling platform.

11. The cassette handling device of claim 9, wherein the transfer device couples to the cassette by vacuum pressure, mechanical interlock, magnetic force, pneumatic force, or electrostatic force.

12. A magazine for storing cassettes for radiolabeled compound synthesis comprising:

an unshielded housing comprising a plurality of slots configured to accommodate a microfluidic synthesis cassette;

a plurality of microfluidic synthesis cassettes disposed respectively in the plurality of slots, wherein the plurality of microfluidic synthesis cassettes comprise non-radioactive reagents to generate a radiolabeled compound when reacted with a radioactive species; and a coupling configured to couple the magazine to a shielded cassette handling platform, wherein the coupling is configured to allow advancement of the plurality of microfluidic synthesis cassettes into the shielded cassette handling platform.

13. The magazine of claim 12, wherein the plurality of microfluidic synthesis cassettes are arranged in a stack.

14. The magazine of claim 12, wherein the plurality of microfluidic synthesis cassettes are arranged about an axis of rotation of the magazine.

15. The magazine of claim 12, wherein the magazine is configured to automatically rotate or shake the plurality of microfluidic synthesis cassettes.

16. The magazine of claim 12, wherein the magazine comprises an on-deck position coupled to the shielded cassette handling platform, wherein only one of the plurality of microfluidic synthesis cassettes associated with the on-deck position is permitted to advance into the shielded cassette handling platform.

17. The magazine of claim 16, comprising a spring-loaded device that advances one of the plurality of microfluidic synthesis cassettes into the on-deck position in series.

18. A cassette handling device for dispensing cassettes for radiolabeled compound synthesis comprising:

a magazine comprising an unshielded housing comprising a plurality of slots configured to accommodate microfluidic synthesis cassettes;

a plurality of microfluidic synthesis cassettes disposed respectively in the plurality of slots, wherein the plurality of microfluidic synthesis cassettes comprise non-radioactive reagents; and a coupling configured to couple the cassette handling device to a cassette handling platform, wherein the coupling is configured to allow advancement of the plurality of microfluidic synthesis cassettes into the cassette handling platform, wherein the cassette handling platform is configured to operatively couple to a radiosynthesis device, and wherein the radio synthesis device is shielded and the cassette handling device is unshielded.

19. The cassette handling device of claim 18, comprising two microfluidic synthesis cassettes that are configured to generate different radiolabeled compounds.

20. The cassette handling device of claim 18, comprising a memory storing one or more routines; and a processing component configured to execute the one or more routines stored in the memory, wherein the one or more routines, when executed by the processing component causes acts to occur, comprising:
receiving a user input;
accessing identification information related to the microfluidic synthesis cassettes;
comparing the user input to the identification information; and
selecting a microfluidic synthesis cassette from the plurality of microfluidic synthesis cassettes based on the comparing.

* * * * *